United States Patent
Yoon et al.

(10) Patent No.: US 7,105,022 B2
(45) Date of Patent: Sep. 12, 2006

(54) IMPLANTABLE LEFT VENTRICULAR ASSIST DEVICE WITH CYLINDRICAL CAM

(75) Inventors: Gul Joong Yoon, Gwangmyong (KR); Han Sang Cho, Seoul (KR)

(73) Assignee: Biomedlab Co., Ltd., Seoul (KR)

( * ) Notice: Subject to any disclaimer, the term of this patent is extended or adjusted under 35 U.S.C. 154(b) by 691 days.

(21) Appl. No.: 10/069,750

(22) PCT Filed: Feb. 23, 2001

(86) PCT No.: PCT/KR01/00277

§ 371 (c)(1),
(2), (4) Date: May 28, 2002

(87) PCT Pub. No.: WO01/97877

PCT Pub. Date: Dec. 27, 2001

(65) Prior Publication Data

US 2002/0165425 A1    Nov. 7, 2002

(30) Foreign Application Priority Data

Jun. 22, 2000    (KR) ................. 2000-34576

(51) Int. Cl.
*A61M 1/12*    (2006.01)
(52) U.S. Cl. .................................. 623/3.17
(58) Field of Classification Search ............ 600/16, 600/17; 623/3.1, 3.11, 3.13, 3.14, 3.16, 3.17, 623/3.18, 3.19
See application file for complete search history.

(56) References Cited

U.S. PATENT DOCUMENTS

| | | | | |
|---|---|---|---|---|
| 3,896,501 A | * | 7/1975 | Bifano et al. | 623/3.18 |
| 4,822,356 A | * | 4/1989 | Chareire et al. | 623/3.18 |
| 5,041,132 A | * | 8/1991 | Miyata | 623/3.18 |

* cited by examiner

*Primary Examiner*—George R. Evanisko
(74) *Attorney, Agent, or Firm*—F. Chau & Associates, LLC

(57) ABSTRACT

An implantable left ventricular assist device using a cylindrical cam is provided, which is produced in a compact and module form and implanted in a patient who suffers from an acute cardiac insufficiency, to thereby enable oxygen to be supplied smoothly toward the heart of the patient and reconstruct the declined function of the heart. The implantable left ventricular assist device includes an actuator for generating a linearly reciprocating driving force, a pusher plate which performs a linearly reciprocating motion by the actuator, a blood sac which is contracted and expanded due to compression by reciprocating the pusher plate and the restoration of a sac itself, and a chamber for accommodating the blood sac, the pusher plate and the actuator, combining the same physically, and protecting the same within the body of a patient. The implantable left ventricular assist device is produced in the compact and module form and is safely and simply implanted in a patient who suffers from an acute cardiac insufficiency. The implantable left ventricular assist device assists a reduced blood amount of aorta, increases the blood amount of aorta, enables oxygen to be supplied smoothly toward the heart of the patient, and then reconstructs the declined function of the heart. Thus, an effect of expediting a recovery of the lowered heart function can be obtained.

6 Claims, 8 Drawing Sheets

US 7,105,022 B2

IMPLANTABLE LEFT VENTRICULAR ASSIST DEVICE WITH CYLINDRICAL CAM

DESCRIPTION

1. Technical Field

The present invention relates to a ventricular assist device which is implanted for a patient who suffers from a heart disease in order to assist the patient's heart function, and more particularly, to an implantable left ventricular assist device using a cylindrical cam which is produced in a compact and module form and implanted in a patient who suffers from an acute cardiac insufficiency, to thereby enable oxygen to be supplied smoothly toward the heart of the patient and reconstruct a declined function of the heart.

2. Background Art

In general, as eating habits of people are modernized and westernized, fat and high protein food is excessively taken. Also, a drinking amount increases and a smoking ratio rises up. At the same time, people are exposed to take polluted air due to an atmosphere pollution. Accordingly, the heart disease occurs much in the modernizers under the circumstances. In the case that the function of the heart is not performed well due to the heart disease, a device replacing the function of the heart is used to assist the heart function. As an existing heart assist device, a large heart assist device is provided and used outside of the body of the patient. Accordingly, it is burdensome to use the large heart assist device and inconvenient to carry it, which limits the behavior of the patient. To overcome this problem, a ventricular assist device which becomes compact to a somewhat degree so as to be explanted to the body of a patient has been developed. However, this explantable ventricular assist device cannot solve inconvenience of use. Thus, it is not possible for a patient to carry and use it conveniently. As a result, an implantable left ventricular assist device using a cylindrical cam has been developed to replace the explantable left ventricular assist device in order to enhance the quality of the patient's life. This implantable left ventricular assist device using a cylindrical cam is also coarse, difficult to operate it in the patient body and inconvenient to use it.

DISCLOSURE OF INVENTION

To solve the above problems, it is an object of the present invention to provide an implantable left ventricular assist device using a cylindrical cam, which is produced in a compact and module form and safely and simply implanted in a patient who suffers from an acute cardiac insufficiency, to thereby assist a reduced blood amount of aorta, increase the blood amount of aorta, enable oxygen to be supplied smoothly toward the heart of the patient, and then reconstruct the declined function of the heart.

To accomplish the above object of the present invention, there is provided an implantable left ventricular assist device using a cylindrical cam which is implanted to a heart-diseased patient to assist the heart, the implantable left ventricular assist device comprising:

an actuator for generating a linearly reciprocating driving force; a pusher plate which performs a linearly reciprocating motion by the actuator; a blood sac which is contracted and expanded due to compression by reciprocating the pusher plate and the restoration of a sac itself; and a chamber for accommodating the blood sac, the pusher plate and the actuator, combining the same physically, and protecting the same within the body of a patient.

The implantable left ventricular assist device using a cylindrical cam is implanted in the patient's body to play a role of an assist function of the heart, which is connected to a battery located outside of the body, a controller and a vent line, to receive power and then be driven and controlled.

BRIEF DESCRIPTION OF DRAWINGS

The above object and other advantages of the present invention will become more apparent by describing the preferred embodiment thereof in more detail with reference to the accompanying drawings in which.

BEST MODE FOR CARRYING OUT THE INVENTION

A preferred embodiment of the present invention will be described with reference to the accompanying drawings.

Figure 1:
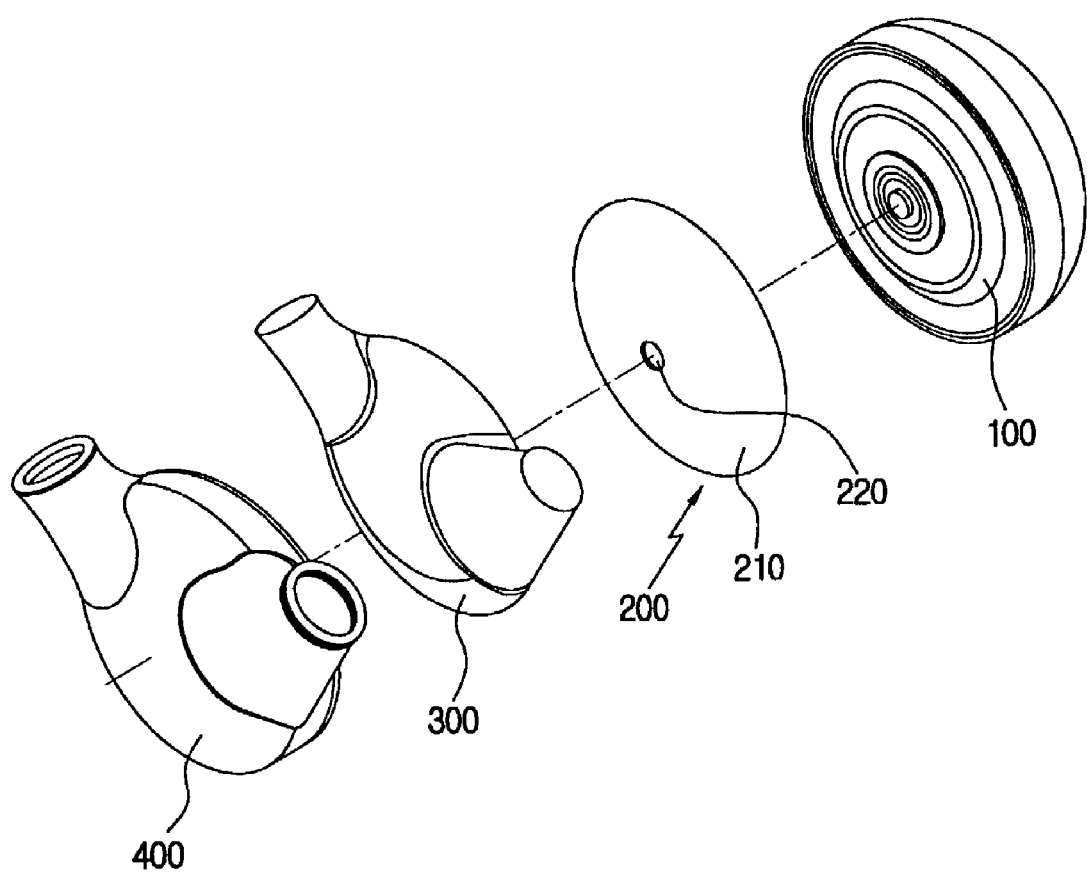
FIG. 1 is an exploded perspective view schematically shown an implantable left ventricular assist device using a cylindrical cam according to the present invention.
Figure 2:
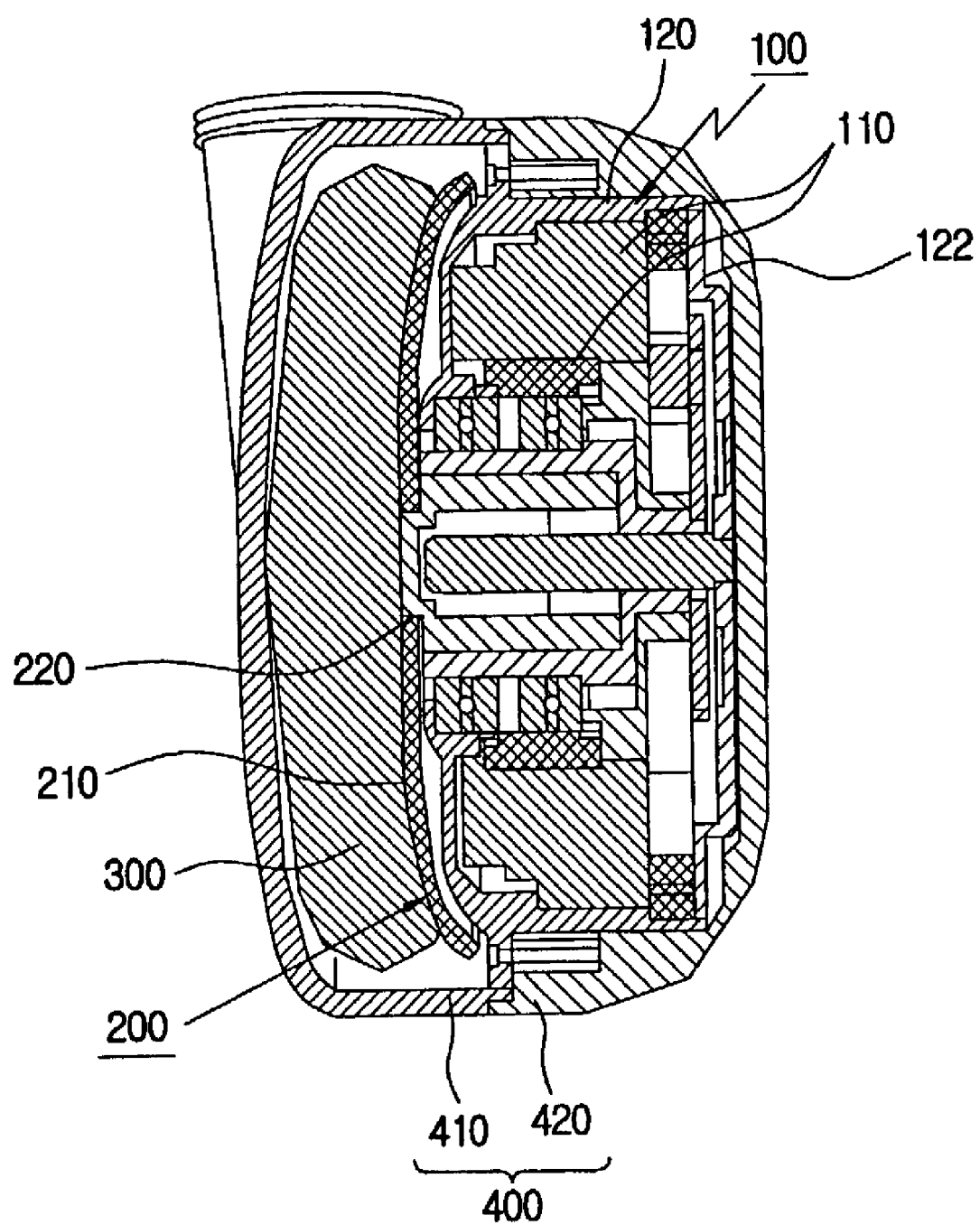
FIG. 2 is an assembled sectional view showing the implantable left ventricular assist device using a cylindrical cam according to the present invention shown in FIG. 1.

FIG. 1 is an exploded perspective view schematically shown an implantable left ventricular assist device using a cylindrical cam according to the present invention. FIG. 2 is an assembled sectional view of FIG. 1.

The implantable left ventricular assist device includes an actuator 100 for generating a driving force enabling the blood to flow, a pusher plate 200 for transferring the driving force generated from the actuator 100, and a blood sac 300 which is contracted and expanded due to the periodical compression and self-restoration by the pusher plate 200, to thereby flow the blood in and out in correspondence to the ventricle of a natural heart. In addition, the implantable left ventricular assist device includes a chamber 400 for accommodating the actuator 100, the pusher plate 200 and the blood sac 300, combining the same physically, maintaining a predetermined shape, and playing a role of a structural assembly in the body of a patient. The chamber 400 includes a front chamber 410 for accommodating and protecting the blood sac 300 and the pusher plate 200, and a rear chamber 420 for accommodating and protecting the actuator 100.

The actuator 100 converts the torque of a motor 110 installed therein into a linearly driving force to thereby make the pusher plate 200 move back and forth, of which the structure and principle will be described in more detail with reference to FIGS. 3 and 4. In the pusher plate 200 moving back and forth by the actuator 100, a pusher face 210 corresponding to the blood sac 300 forms a substantially flat circular plate shape, on the center of which an engagement hole 220 combined with the movable part of the actuator 100 is perforated. The blood sac 300 is made of an elastic material and is compressed and self-restored by means of a linearly reciprocating motion of the pusher plate 200 to be contracted and relaxed like the heart. For this reason, the blood sac 300 makes the blood flow in during relax, and flow out during contract, to supply the blood to the necessary portions of the human body.

Figure 3:
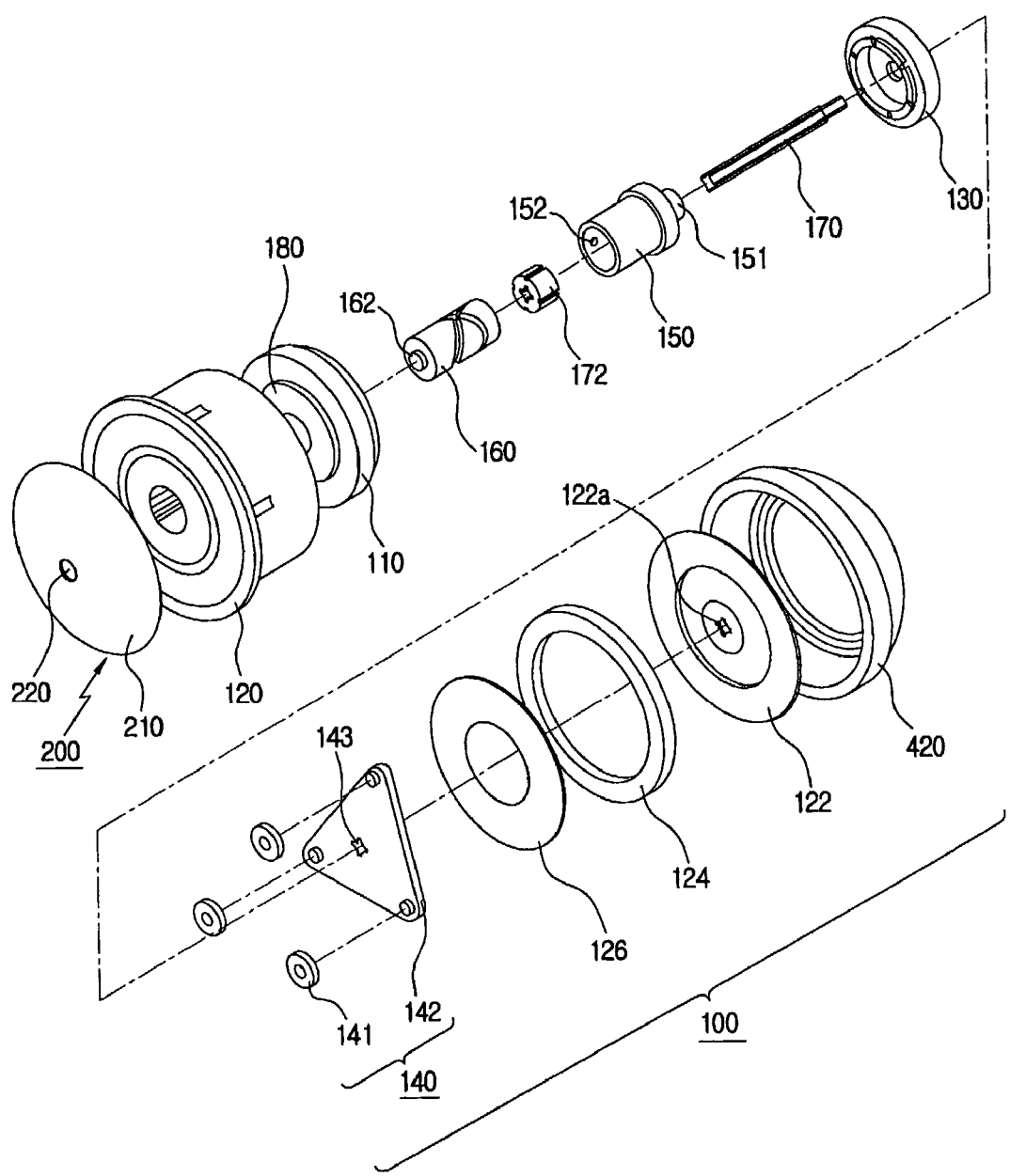
FIG. 3 is an exploded perspective view showing an actuator and a pusher plate in the present device.
Figure 4:
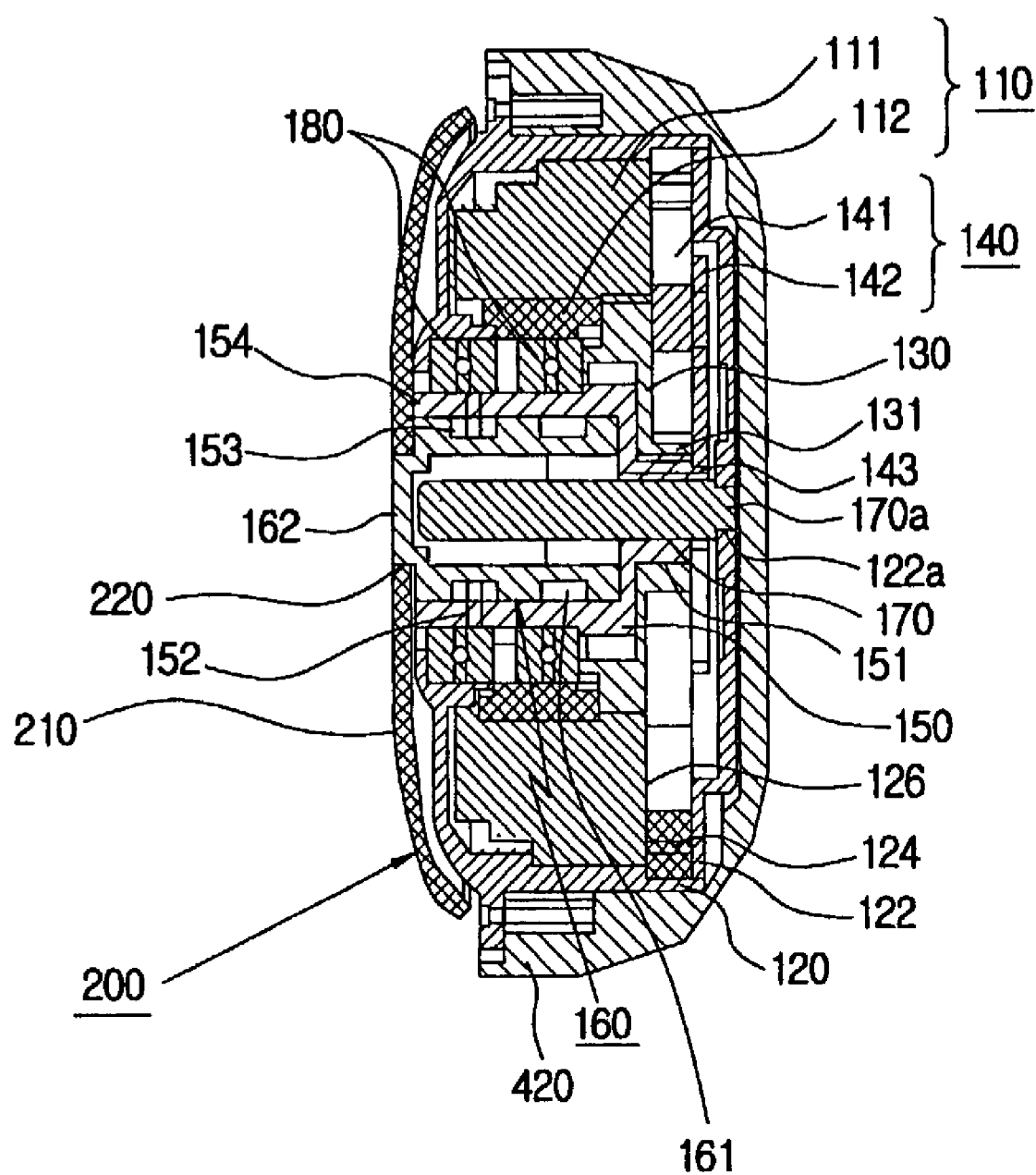
FIG. 4 is an assembled perspective view showing the actuator and the pusher plate in the present device shown in FIG. 3.

FIG. 3 is an exploded perspective view showing an actuator and a pusher plate in the present device. FIG. 4 is an assembled perspective view showing the actuator and the pusher plate in the present device shown in FIG. 3.

The actuator 100 includes constructional elements such as a motor 110, a major axis 130, a planetary gear body 140, a minor axis 150, a cylindrical cam 160 and a guiding axle 170, and a case 120 and a rear cover 122 in which the constructional elements are accommodated and fixed. The actuator 100 is accommodated and fixed in the rear chamber 420. The motor 110 is mounted and fixed inside the case 120. A stator 111 of the motor 110 is fixed to the case 120. A rotor 112 is situated adjacent to the stator 111. The rotor 112 is connected with the major axis 130. The major axis 130 is formed of a thin vessel shape. The rear side of the major axis is protruded with a small diameter to form a major axis gear 131. The planetary gear 141 is threadedly engaged with the major axis gear 131 to receive a torque. The planetary gear 141 is fixed on the support plate 142, in which the planetary gear 141 turns round on its axis and revolves the center of the support plate 142. Thus, the support plate 142 rotates on its axial center finally. As described above, the planetary gear 141 and the support plate 142 rotating and revolving form a planetary gear assembly 140. Conclusively, the torque of the motor 110 is reduced through the planetary gear assembly 140 engaged with the major axis gear 131 and the reduced torque is output. For this purpose, a ring gear 124 is fixed inside the case 120 which closely contacts the planetary gear 141, and the planetary gear 141 moves along the ring gear 124 while revolving the ring gear 124. The ring gear 124 closely contacts the rear cover 122 and fixed thereto, in which an annular support circular plate 126 is disposed between the ring gear 124 and the motor 110, in order to divide the ring gear 124 and the motor 110, and attach and fix the ring gear 124 closely to the rear cover 122. The detailed description with respect to the planetary gear assembly 140 will be given with reference to FIG. 5.

A cross-shaped fixing hole 143 is formed on the center of the support plate 142 in the planetary gear assembly 140. A fixing portion 151 of the minor axis 150 is inserted and fixed into the fixing hole 143. Thus, the minor axis 150 rotates according to the torque of the support plate 142. The minor axis 150 includes a small vessel-shaped fixing portion 151 fixed in the center of the planetary gear assembly 140 and a cylindrical portion 154 forming a large cylinder from the fixing portion 151, in which roller fixing holes 152 are symmetrically formed on predetermined positions and rollers 153 are mounted. A cylindrical cam 160 is inserted inside the cylindrical portion 154, cam grooves 161 are formed on the outer circumferential surface of the inserted cylindrical cam 160, and then a predetermined portion of the roller 153 is inserted. The roller 153 moves along the cam groove 161 according to the rotation of the minor axis 150, and thus the cylindrical cam 160 moves back and forth. In particular, the cam grooves 161 are symmetrically formed on the outer circumferential surface of the cylindrical cam 160. Accordingly, the rollers 153 and the cylindrical cam 160 contact at two places distanced by 180°. As described above, if the cylindrical cam 160 moves back and forth, the pusher plate 200 combined with the cylindrical cam 160 performs a reciprocating motion back and forth. For this, a combination protrude 162 protrudes on the cylindrical cam 160 and inserted into and combined with a combination groove 220 formed in the center of the pusher plate 200.

In particular, a guiding axle 170 is inserted and penetrated into the cylindrical cam 160 in order to guide a linearly reciprocating motion of the cylindrical cam 160. The guiding axle 170 also penetrates the fixing portion 151 of the minor axis 150 which is located in the rear portion of the cylindrical cam 160, and then inserted and fixed into a center fixing hole 122a of the rear cover 122. A guiding piece 172 is disposed between the guiding axle 170 and the cylindrical cam 160, and guides the cylindrical cam 160 to perform a linearly reciprocating motion accurately along the guiding axle 170. The detailed description thereof will be given with reference to FIGS. 6A and 6B. Here, a reference numeral 180 denotes bearings.

Figure 5:
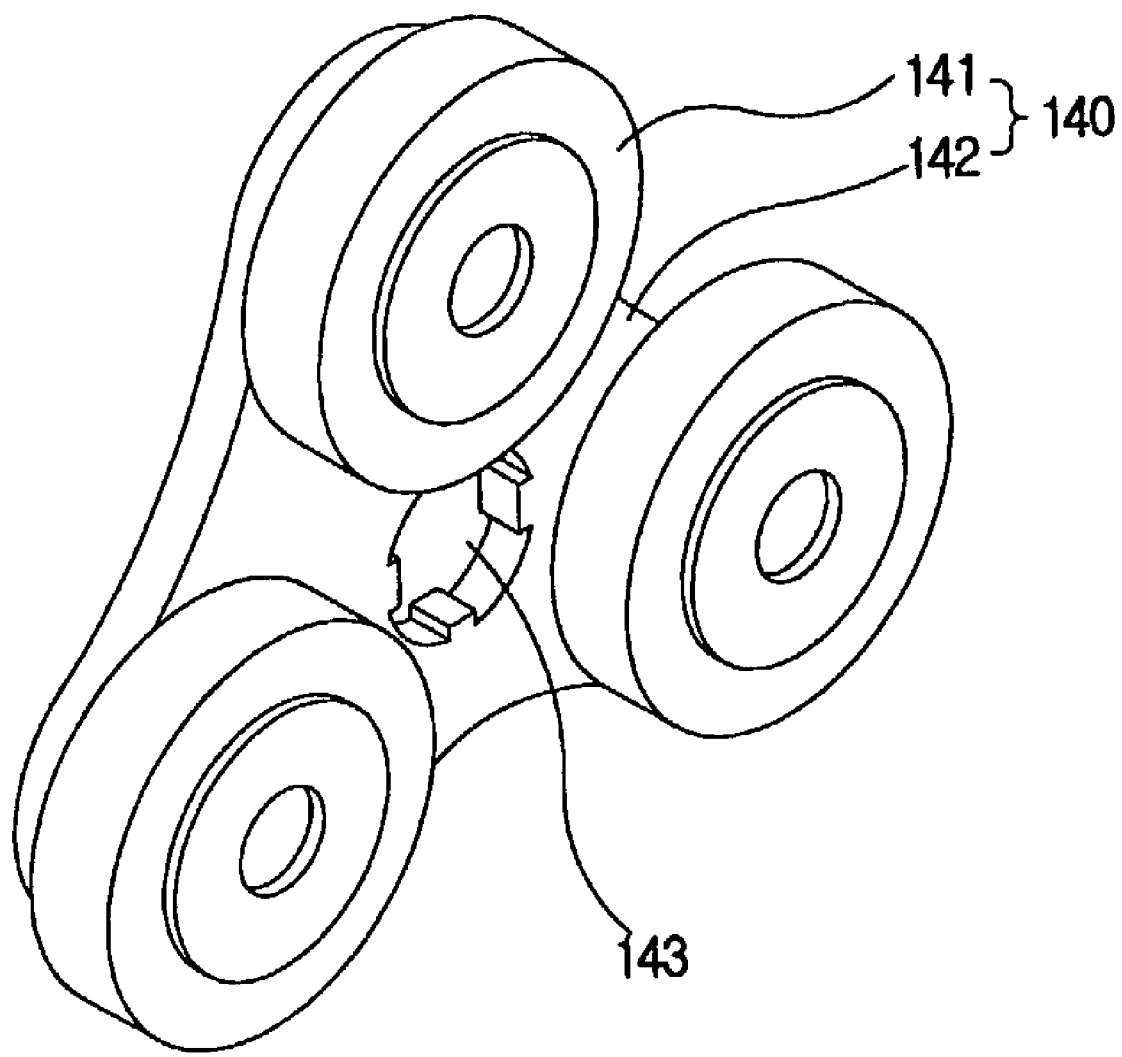
FIG. 5 is a perspective view showing the state where a planetary gear and a support plate are combined with each other.

FIG. 5 is a perspective view showing the state where a planetary gear and a support plate are combined with each other.

As shown in FIG. 5, the planetary gear assembly 140 for reducing the driving force of the above-described major axis (not shown) and outputting the driving force includes three planetary gears 141 and the support plate 142 for fixing the planetary gears 141 by equi-distance therefrom. In particular, the three planetary gears 141 are rotatably fixed so that they rotate on the support plate 142 on their axes, respectively. Therefore, if three planetary gears 141 receive a torque from the major axis gear and rotate on their axes, the torque enables the planetary gears 141 to move along the ring gear due to the threaded engagement with the ring gear in the case (not shown), and revolve on the center of the three planetary gears 141, that is, the center of the support plate 142. Finally, the support plate 142 rotates to thereby obtain the result that the driving force of the motor is reduced and the reduced driving force is output for the support plate 142. As described above, the reduced torque of the support plate 142 is transferred to the minor axis combined to the fixing hole 143.

Figure 6A:
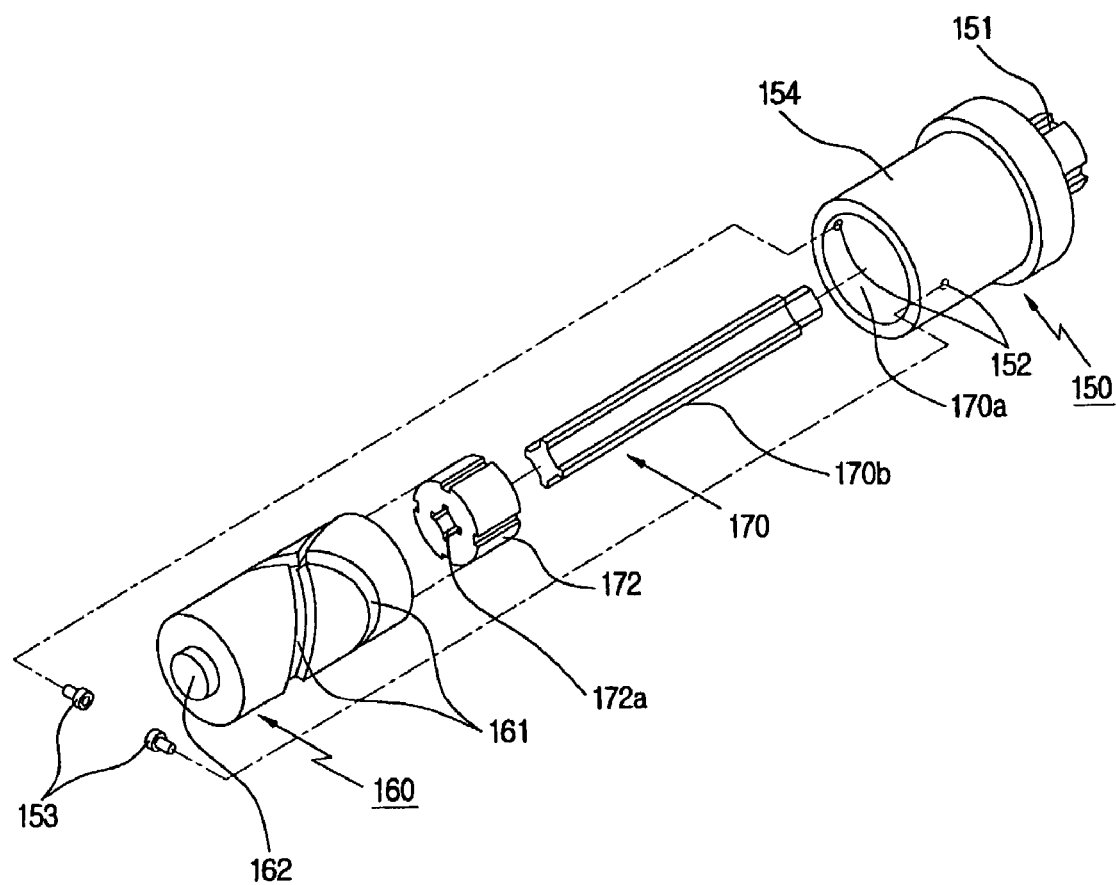
FIG. 6A is an exploded perspective view of a minor axis and a cylindrical cam in the present device.
Figure 6B:
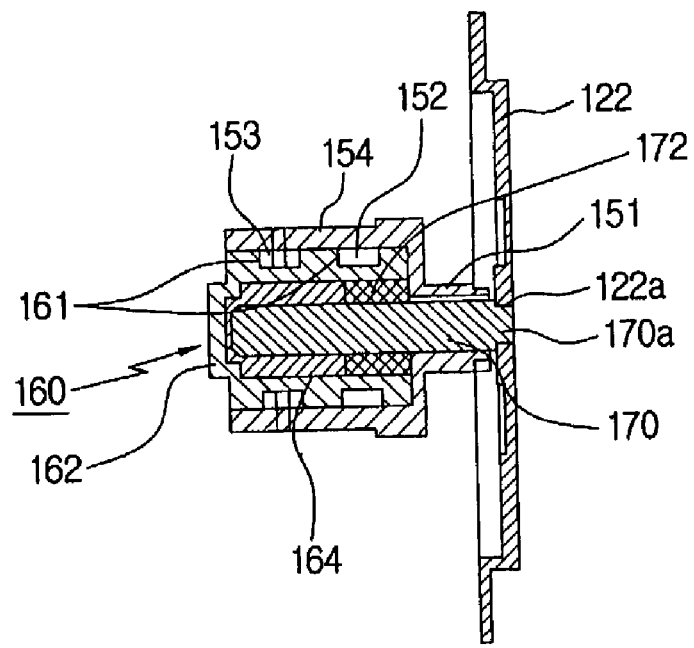
FIGS. 6B and 6C are sectional views showing the state where the minor axis and the cylindrical cam are combined with each other.
Figure 6C:
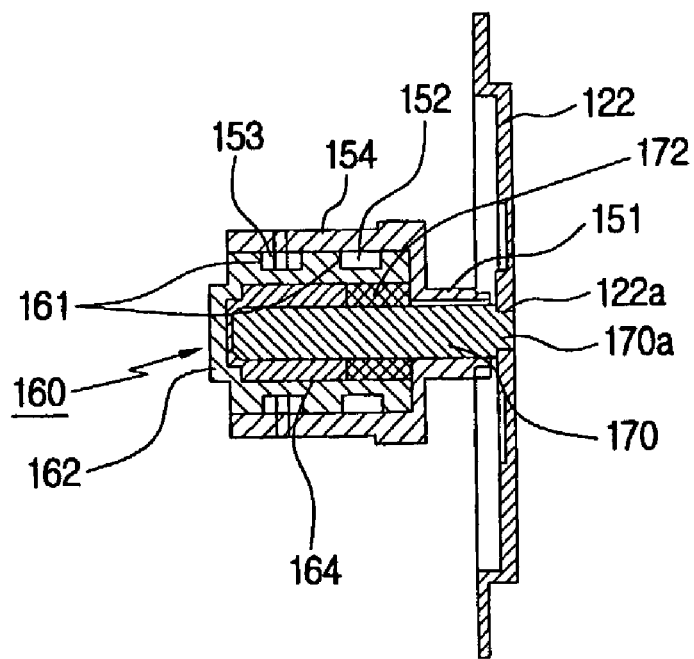
Figure 7:
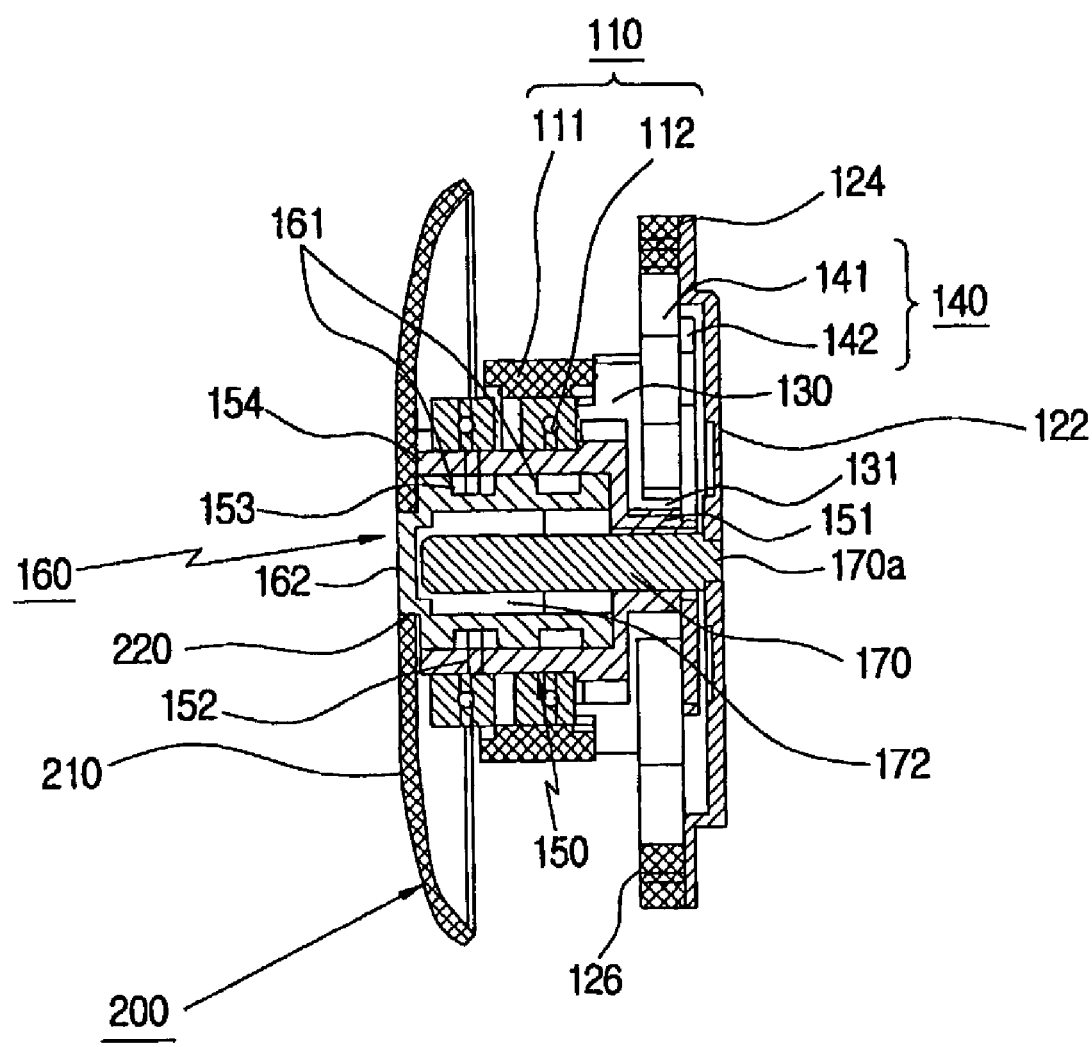
FIG. 7 is a partial sectional view showing essential elements in order to explain an operation between the minor axis and the cylindrical cam and a relational operation of a pusher plate in the present device.

FIG. 6A is an exploded perspective view of a minor axis and a cylindrical cam in the present device. FIGS. 6B and 6C are sectional views showing the state where the minor axis and the cylindrical cam are combined with each other. Also, FIG. 7 is a partial sectional view showing essential elements in order to explain an operation between the minor axis and the cylindrical cam and a relational operation of a pusher plate in the present device.

The minor axis 150 includes the small vessel-shaped fixing portion 151 fixed to the center of the above-described planetary gear assembly. From the fixing portion 151 is extended the cylindrical portion 154 having a large cylindrical shape, in which two roller fixing holes 152 facing each other are formed on predetermined positions, and the rollers 153 are mounted. The cylindrical cam 160 is inserted into the cylindrical portion 154. The double cam grooves 161 crossed with each other are formed on the outer circumferential surface of the cylindrical cam 160, in which the rollers 153 are inserted in predetermined positions and then the cylindrical cam 160 and the minor axis 150 are combined with each other. Thus, if the minor axis 150 rotates, the two rollers 153 move on the cam grooves 161 to thereby enable the cylindrical cam 160 to move back and forth. For this purpose, the cam grooves 161 travel around the outer circumferential surface of the cylindrical cam 160 in an X-crossed form, and are formed concavely thereon. Each of the crossed cam grooves forms a sine waveform. Therefore, the rollers 153 move along the cam grooves 161 according to the rotation of the minor axis 150. Accordingly, the cylindrical cam 160 moves back and forth by displacement of the grooves (that is a distance in the axial direction) in the axial direction. A stroke of the cylindrical cam 160 is determined according to the distance in the axial direction of the cam grooves 161.

A combining protrude 162 is formed in the cylindrical cam 160, in order to combine the cylindrical cam 160 with the pusher plate 200 and move the pusher plate 200 back and forth according to the linearly reciprocating motion of the cylindrical cam 160, and a combining groove 220 is formed in the center of the pusher plate 200 corresponding to the cylindrical cam 160, so that the combining protrude 162 and the combining groove 220 are fixedly combined with each other. Also, an axial tubular hole 164 is formed inside the cylindrical cam 160, and the guiding axle 170 is inserted at predetermined positions, in order to guide a linear motion of the cylindrical cam 160 safely. The guiding axle 170 penetrates the minor axis 150 and then is fixed to the center fixing hole 122a of the rear cover 122. The cross-shaped fixing hole 122a is perforated in the center portion of the rear cover 122 of a circular plate type, and a cross-shape mount 170a is formed in the post end of the guiding axle 170 corresponding to the center fixing hole 122a. Also, four guiding protrudes 170b are formed along the axial line of the guiding axle 170. The guiding piece 172 is inserted into the guiding axle 170, and inserted and fixed inside the cylindrical cam 160. The guiding piece 172 is guided linearly since guiding grooves 172a is formed in correspondence to guiding protrude 170b in the guiding axle 170. By doing so, the cylindrical cam 160 in which the guiding piece 172 is fixed is accurately and safely guided on the guiding axle 170 to thereby perform a linear motion.

Now, the operational principle of the left ventricular assist device according to the present invention will be described in detail with reference to the accompanying drawings.

If the present device is implanted in the human body and powered on, the motor 110 in the actuator 100 is driven. Then, the major axis 130 rotates in which the rotor 112 of the motor 110 is fixed. Accordingly, the planetary gears 141 threadedly engaged with the major axis gear 131 rotate and move along the ring gear 124 in the case 120. Then, the support plate 142 rotates in which the planetary gears 141 are fixed. The rotational velocity of the major axis 130 is reduced and the reduced velocity is output to the minor axis 150 fixed to the center of the support plate 142. Thus, the minor axis 150 rotates and the rollers 153 fixed to the minor axis 150 move along the cam groove 161 of the cylindrical cam 160 according to the rotation of the minor axis 150, to thereby perform a reciprocating motion back and forth. Here, the cylindrical cam 160 is linearly guided along the guiding axle 170 by the guiding piece 172 and performs a linearly reciprocating motion stably. Then, the pusher plate 200 fixed to the cylindrical cam 160 performs a reciprocating motion to contract or expand the blood sac 300 and to accordingly take the blood in and out to be supplied to a necessary portion of the human body.

INDUSTRIAL APPLICABILITY

As described above, the implantable left ventricular assist device using a cylindrical cam according to the present invention is produced in a compact and module form, and safely and simply implanted in a patient who suffers from an acute cardiac insufficiency, to thereby assist a reduced blood amount of aorta, increase the blood amount of aorta and enable oxygen to be supplied smoothly toward the heart of the patient and reconstruct the declined function of the heart. Thus, the present invention has an effect of expediting a recovery of the lowered heart function.

The invention claimed is:

1. An implantable left ventricular assist device which is implanted to a heart-diseased patient to assist the heart, the implantable left ventricular assist device comprising:
   an actuator for generating a linearly reciprocating driving force, wherein the actuator comprises a motor for generating a torque and a planetary gear assembly for reducing the torque of the motor;
   a pusher plate which performs a linearly reciprocating motion by the actuator;
   a blood sac which is contracted and expanded due to compression by reciprocating the pusher plate and the restoration of the blood sac; and
   a chamber for accommodating the blood sac, the pusher plate and the actuator, combining the same physically, and protecting the same within the body of a patient,
   wherein said actuator further comprises:
   a major axis which is driven by the motor, including a major axis gear at an end portion of the major axis, wherein the planetary pear assembly is threadedly engaged with the major axis gear;
   a minor axis, including a vessel-shaped fixing portion built in the center of the planetary gear assembly, and a cylindrical portion within which a pair of rollers are mounted on a predetermined position, while having a large cylindrical shape with respect to the fixing portion;
   a cylindrical cam which is inserted into the cylindrical portion of the minor axis, combined with the pusher plate, provided with a double cam groove along which the rollers move on an outer circumferential surface of the minor axis, and performs a linearly reciprocating motion according to the rotation of the minor axis; and
   a case and a rear cover which is provided with a ring gear threadedly engaged with the planetary gear assembly externally in a corresponding position, enables the motor and the minor axis to rotate together, and accommodates the cylindrical cam, the minor axis, the planetary gear assembly, the major axis and the motor.

2. The implantable left ventricular assist device of claim 1, wherein said planetary gear assembly comprises three planetary gears which are threadedly engaged with the major axis gear to rotate, and a support plate in which the planetary gears are rotatably fixed and of which the minor axis is fixed in the center.

3. The implantable left ventricular assist device of claim 1, wherein said cam grooves are in an X-crossed form while forming a substantially sine waveform in the axial direction according to the circumference of the cam outer circumferential surface and have a symmetrical structure with each other.

4. The implantable left ventricular assist device of claim 1, wherein said actuator further comprises a guiding axle which is substantially vertically fixed to the center of the rear cover, and
   a guiding piece externally disposed on the guiding axle and fixed to the cylindrical cam, for guiding a linearly reciprocating motion of the cylindrical cam.

5. The implantable left ventricular assist device of claim 4, wherein a plurality of guiding protrudes are provided along the axial line on an outer circumferential surface of the guiding axle, and guiding grooves are formed so that the guiding protrudes are inserted in the opposite positions of the guiding piece corresponding to the guiding protrudes.

6. The implantable left ventricular assist device of claim 4, wherein a plurality of guiding protrudes are provided along the axial line on an outer circumferential surface of the guiding axle, and guiding grooves are formed so that the guiding protrudes are inserted in the opposite positions of the guiding piece corresponding to the guiding protrudes.

* * * * *